United States Patent
Kimura et al.

(10) Patent No.: US 6,265,412 B1
(45) Date of Patent: Jul. 24, 2001

(54) MINOXIDIL COMPOSITIONS FOR EXTERNAL USE

(75) Inventors: Fuminori Kimura, Omiya; Kenichi Suzuki, Urawa; Koji Imamura, Kasukabe; Takako Okajima, Gyoda, all of (JP)

(73) Assignee: Taisho Pharmaceutical Co., Ltd. (JP)

( * ) Notice: Subject to any disclaimer, the term of this patent is extended or adjusted under 35 U.S.C. 154(b) by 0 days.

(21) Appl. No.: 09/700,741

(22) PCT Filed: May 22, 1999

(86) PCT No.: PCT/JP99/02722

§ 371 Date: Nov. 20, 2000

§ 102(e) Date: Nov. 20, 2000

(87) PCT Pub. No.: WO99/61059

PCT Pub. Date: Dec. 2, 1999

(30) Foreign Application Priority Data

May 26, 1998 (JP) .................................................. 10-144598

(51) Int. Cl.$^7$ ...................... A61K 31/505; A61K 31/415; A61K 31/135; A61K 31/13

(52) U.S. Cl. .......................... 514/273; 514/396; 514/646; 514/670

(58) Field of Search ..................................... 514/273, 396, 514/646, 670

(56) References Cited

U.S. PATENT DOCUMENTS

4,888,354 * 12/1989 Chang et al. .
5,015,470 5/1991 Gibson ................................... 424/70

FOREIGN PATENT DOCUMENTS

1003001 10/1991 (BE) .
63-166823 7/1988 (JP) .
07053338 * 2/1995 (JP) .
10167934 * 6/1998 (JP) .

* cited by examiner

*Primary Examiner*—William R. A. Jarvis
*Assistant Examiner*—Vickie Kim
(74) *Attorney, Agent, or Firm*—Lorusso & Loud

(57) ABSTRACT

There is provided a composition for external use with a reduced skin irritation comprising minoxidil and 0.01 to 2 parts by weight of at least one antihistaminic agent selected from the group consisting of chlorphenylamine maleate, diphenylimidazole, diphenhydramine and a salt thereof per 1 part by weight of minoxidil.

1 Claim, No Drawings

MINOXIDIL COMPOSITIONS FOR EXTERNAL USE

This application is a 371 of PCT/JP99/02722 filed May 22, 1999.

TECHNICAL FIELD

The present invention relates to a minoxidil-containing composition for external use which, when applied onto skin, has a reduced skin irritation.

BACKGROUND ART

Minoxidil (2,4-diamino-6-piperidino-pyrimidine-3-oxide), a therapeutic agent of hypertension, was found to cause hypertrichosis as a side-effect, thereby it has recently been used as an effective component in the compositions for external use for the purpose of therapy of genital baldness or seborrheic baldness. However, it is reported that minoxidil-containing compositions for external use, when used, rarely have side-effects such as skin irritation (Contact Dermatitis 1987:17:44). Generally, glycols (e.g., glycerol) and anti-inflammatory agents (e.g., glycyrrhetic acid) are used for healing the drug-caused skin irritation, but they have an insufficient inhibition effect on the skin irritation when used together with minoxidil.

DISCLOSURE OF THE INVENTION

As a result of extensive researches in order to overcome the above problem, the present inventors have found that the skin irritation as a side-effect of the minoxidil-containing composition for external use is surprisingly reduced by combining the minoxidil-containing composition for external use with an antihistaminic agent which has been used as a medicine to relieve itching, thereby the present invention has been accomplished. That is, the present invention is directed to a composition for external use comprising minoxidil and an antihistaminic agent.

Preferably, the composition for external use according to the present invention contains minoxidil in an amount of from 0.1 to 5% by weight, and an antihistaminic agent in an amount of from 0.01 to 5% by weight. When the amount of minoxidil is less than 0.1% by weight, the therapeutic effect may not be expected, and when it exceeds 5% by weight, there may be a risk that a lowering action of blood pressure occurs. Furthermore, when the amount of the antihistaminic agent is less than 0.01% by weight, the inhibition effect of skin irritation may be weak, on the contrary, when it exceeds 5% by weight, there may be a possibility that the antihistaminic agent causes skin irritation by itself. With regard to the amount ratio of minoxidil and the antihistaminic agent, it is preferable that the amount of the antihistaminic agent ranges from 0.01 to 2 parts by weight per 1 part by weight of minoxidil.

Preferred examples of the antihistaminic agent in the present invention are chlorphenylamine maleate, diphenylimidazole, diphenhydramine and a salt thereof. The amount of the antihistaminic agent to be incorproated ranges preferably from 0.01 to 1 part by weight for chlorphenylamine maleate or diphenylimidazole and from 0.02 to 2 parts by weight for diphenhydramine or a salt thereof, respectively, per 1 part by weight of minoxidil. These antihistaminic agents may be also properly used in combination.

In order to further reduce the skin irritation of the composition for external use of the present invention, it is preferable to further incorporate an anti-inflammatory agent thereinto. Suitable anti-inflammatory agent includes glycyrrhetic acid, glycyrrhizic acid, a salt thereof, dimethylisopropylazulene and sodium azulenesulfonate. The amount of the anti-inflammatory agent is not particularly limited unless the effect of the present invention is degraded thereby, but preferably it is in the range of from 0.05 to 1% by weight.

The composition for external use according to the present invention can contain effective components other than the above-mentioned effective components. Specific examples thereof include carpronium chloride, benzyl nicotinate, tocopherol acetate, urea, salicylic acid, sodium hyaluronate, chondroitin sulfuric acid, crude drugs (e.g., swertia, panax ginseng, capsicum, plant worm vegetative wags, saffron or extracts thereof), antimicrobial agents (e.g., chlorhexidine gluconate, isopropyl methyl phenol, quaternary ammonium salts or hinokitiol).

The composition for external use of the present invention, if necessary, can contain components which are ordinarily used for making preparations for external use in a desired form such as liquids, creams, ointments, gels or aerosols; and specific examples of such components are water, lower alcohols, solubilizers (e.g., fatty acid esters, polyhydric alcohols, polyhydric alcohol fatty acid esters, medium chain fatty acid glycerides, vegetable oils, animal oils, alkyl glycerol ethers and hydrocarbons), surface active agents (e.g., nonionic surface active agents, lecithin derivatives and high molecular emulsifiers), emulsifying stabilizers, gelling agents, adhesives, anti-oxidants (e.g., dibutylhydroxytoluene and isopropyl gallate), refrigerants (e.g., menthol, mentha oil and camphor), perfumes or dyes.

BEST MODE FOR CARRYING OUT THE INVENTION

The present invention makes it possible to provide a minoxidil-containing composition for external use which has a reduced skin irritation. The present invention is illustrated in more detail with reference to the following examples and test examples.

EXAMPLE 1

| | |
|---|---|
| Minoxidil | 1.0(W/V%) |
| Chlorphenylamine maleate | 0.1 |
| Propylene glycol | 10.0 |
| Denatured ethanol | 60.0 |
| Purified water | Balance to total 100 ml |

The above-mentioned components were stirred and uniformly dissolved to obtain a liquid preparation for external use.

EXAMPLE 2

| | |
|---|---|
| Minoxidil | 1.0(W/V%) |
| Diphenhydramine hydrochloride | 0.2 |
| Glycyrrhetic acid | 0.1 |
| Tocopherol acetate | 0.1 |
| l-Menthol | 0.3 |
| Propylene glycol | 10.0 |
| Denatured ethanol | 60.0 |
| Purified water | Balance to total 100 ml |

The above-mentioned components were stirred and uniformly dissolved to obtain a liquid preparation for external use.

EXAMPLE 3

| | |
|---|---|
| Minoxidil | 5.0(W/W%) |
| Diphenylimidazole | 1.0 |
| Diphenhydramine salicylate | 2.0 |
| Sodium azulenesulfonate | 0.5 |
| Medium chain fatty acid triglyceride | 20.0 |
| Diisopropyl adipate | 5.0 |
| Propylene glycol | 12.0 |
| Polyoxyethylene sorbitan monostearate | 6.0 |
| Sorbitan monostearate | 3.0 |
| Glyceryl monostearate | 8.0 |
| Purified water | Balance to total 100 g |

A cream preparation for external use was obtained from the above-mentioned components according to a conventional method.

EXAMPLE 4

| | |
|---|---|
| Minoxidil | 0.5 (W/W%) |
| Diphenhydramine | 0.02 |
| Dipotassium glycyrrhizinate | 0.1 |
| Dimethylisopropylazulene | 0.01 |
| Polyethylenegylcol monostearate | 5.0 |
| Diisopropyl adipate | 3.0 |
| 1,3-Butylene glycol | 8.0 |
| Polyvinylpyrrolidone | 0.5 |
| Carboxyvinyl polymer | 1.5 |
| Diisopropanolamine | q.s. |
| Denatured ethanol | 30.0 |
| Purified water | Balance to total 100 g |

A gel preparation for external use was obtained from the above-mentioned components according to a conventional method.

EXAMPLE 5

| | |
|---|---|
| Minoxidil | 0.1 (W/W%) |
| Chlorphenylamine maleate | 0.008 |
| Polyethylene sorbitan tristearate | 1.2 |
| Diisopropyl adipate | 2.0 |
| 1,3-Butylene glycol | 1.2 |
| Denatured ethanol | 20.0 |
| Purified water | 15.152 |
| Isopentane | 10.0 |
| Liquefied petroleum gas | 3.0 |
| Dimethyl ether | 47.0 |

An aerosol preparation for external use was obtained from the above-mentioned components according to a conventional method.

TEST EXAMPLE 1

Three subjects who had been identified to induce skin irritation with a minoxidil-containing preparation for external use were each occlusively pasted with a plaster for patch test (mini-size, Torii Pharmaceuticals Co.) which had been spread with 10 µg of each of the liquid preparations produced according to the formulation shown in Table 1. At the same time, no-spread plaster was also pasted as a blank in the same manner. Twenty-four hours later, the plaster was ripped off, and the irritation values were macroscopically judged immediately, 1 hour, 3 hours, 5 hours and 24 hours after ripping. The macroscopic judge was carried out by scoring according to the following criterion.

Macroscopic judge criterion of skin irritation

| | |
|---|---|
| No response | 0 |
| Slight erythema | 1 |
| Distinct erythema | 2 |

The results are shown in Tables 2 to 4.

TABLE 1

| | Example 1 | Comparative Example 1 | Comparative Example 2 | Comparative Example 3 |
|---|---|---|---|---|
| Minoxidil | 1.0 | 1.0 | 1.0 | — |
| Chlorphenylamine maleate | 0.1 | — | — | — |
| Glycyrrhetic acid | — | — | 0.1 | — |
| Propylene glycol | 10.0 | 10.0 | 10.0 | 10.0 |
| Denatured ethanol | 60.0 | 60.0 | 60.0 | 60.0 |
| Purified water | Balance to total 100 ml | Balance to total 100 ml | Balance to total 100 ml | Balance to total 100 ml |

TABLE 2

Patch test results of Subject A

| | Immediately after | After 1 hour | After 3 hours | After 5 hours | After 24 hours |
|---|---|---|---|---|---|
| Example 1 | 0 | 0 | 0 | 0 | 0 |
| Comparative Example 1 | 2 | 2 | 2 | 2 | 2 |
| Comparative Example 2 | 2 | 2 | 2 | 2 | 2 |
| Comparative Example 3 | 1 | 0 | 0 | 0 | 0 |
| Blank | 0 | 0 | 0 | 0 | 0 |

TABLE 3

Patch text results of Subject B

| | Immediately after | After 1 hour | After 3 hours | After 5 hours | After 24 hours |
|---|---|---|---|---|---|
| Example 1 | 1 | 0 | 0 | 0 | 0 |
| Comparative Example 1 | 1 | 1 | 2 | 2 | 2 |
| Comparative Example 2 | 1 | 1 | 1 | 2 | 1 |
| Comparative Example 3 | 1 | 1 | 0 | 0 | 0 |
| Blank | 0 | 0 | 0 | 0 | 0 |

TABLE 4

Patch text results of Subject C

| | Immediately after | After 1 hour | After 3 hours | After 5 hours | After 24 hours |
|---|---|---|---|---|---|
| Example 1 | 0 | 0 | 0 | 0 | 0 |
| Comparative Example 1 | 1 | 1 | 2 | 2 | 1 |
| Comparative Example 2 | 2 | 1 | 2 | 2 | 1 |

TABLE 4-continued

Patch text results of Subject C

| | Immediately after | After 1 hour | After 3 hours | After 5 hours | After 24 hours |
|---|---|---|---|---|---|
| Comparative Example 3 | 0 | 0 | 0 | 0 | 0 |
| Blank | 0 | 0 | 0 | 0 | 0 |

The results shown in Tables 2 to 4 demonstrate that the liquid preparation obtained by Example 1 remarkably lowered the irritation of minoxidil, and it had a lowering grade approximately equal to that of the preparation obtained by Example 3 and blank, both of which do not contain minoxidil. They also confirm that the liquid preparation obtained by Example 1 has a higher inhibition effect on skin irritation than the preparation obtained by Example 2 containing glycyrrhetic acid which is used widely for the inhibition of skin irritation.

INDUSTRIAL APPLICABILITY

There is provided a minoxidil-containing composition for external use which lowers skin irritation.

What is claimed is:

1. A composition for external use consists essentially of 1 part by weight of minoxidil and 0.01 to 2 parts by weight of at least one antihistaminic agent selected from the group consisting of chlorphenylamine maleate, diphenylimidazole, diphenhydramine and a salt thereof.

* * * * *

UNITED STATES PATENT AND TRADEMARK OFFICE
CERTIFICATE OF CORRECTION

PATENT NO. : 6,265,412 B1
DATED : July 24, 2001
INVENTOR(S) : Kimura et al.

It is certified that error appears in the above-identified patent and that said Letters Patent is hereby corrected as shown below:

Column 1,
Line 42, "weight,." should read -- weight, --.

Column 6,
Line 10, "consists" should read -- consisting --.

Signed and Sealed this

Twenty-third Day of April, 2002

Attest:

JAMES E. ROGAN
*Attesting Officer*  *Director of the United States Patent and Trademark Office*